US009377473B2

(12) United States Patent
Lavigne et al.

(10) Patent No.: US 9,377,473 B2
(45) Date of Patent: Jun. 28, 2016

(54) IMMUNOASSAYS AND METHODS OF DETECTING AND MEASURING INTACT FIBROBLAST GROWTH FACTOR 23, AND C-TERMINAL AND N-TERMINAL FRAGMENTS THEREOF

(71) Applicant: Harald Jueppner, Lexington, MA (US)

(72) Inventors: Jeffrey Lavigne, San Clemente, CA (US); Richard Zahradnik, San Clemente, CA (US)

(73) Assignee: Harald Jueppner, Lexington, MA (US)

( * ) Notice: Subject to any disclaimer, the term of this patent is extended or adjusted under 35 U.S.C. 154(b) by 0 days.

(21) Appl. No.: 13/841,800

(22) Filed: Mar. 15, 2013

(65) Prior Publication Data

US 2014/0273013 A1   Sep. 18, 2014

(51) Int. Cl.
*G01N 33/00* (2006.01)
*G01N 33/74* (2006.01)

(52) U.S. Cl.
CPC ............ *G01N 33/74* (2013.01); *G01N 2333/50* (2013.01)

(58) Field of Classification Search
None
See application file for complete search history.

(56) References Cited

U.S. PATENT DOCUMENTS

| 2003/0113816 A1* | 6/2003 | Weitz et al. ..................... 435/7.9 |
| 2005/0106755 A1 | 5/2005 | Zahradnik et al. |
| 2005/0250141 A1* | 11/2005 | Lambert et al. .................. 435/6 |

OTHER PUBLICATIONS

Yamazaki et al.; Anti-FGF23 neutralizing antibodies show the physiological role and strutural features of FGF23; J Bone Mlner Res. 2008, vol. 23(9); p. 1509-18; Abstract p. 1511, col. 2, top paragraph; and p. 152 Fig 1.
Kainos Laboratories, FGF-23 ELISA Kit, Instruction, 2008 (online). [Retrieved on May 20, 2014] from the Internet: URL: http://.kainos.co.jp/eng/products/fgf23_r/fgf23_e_1.html [entire documentation].
IMMUTOPICS_Mouse, Mouse/Rat FGF-23 (C-Term) ELISA Kit, Instruction, Oct. 18, 2013 [online] [Retrieved on May 20, 2014] from Internet: URL: http://www.immutopics.com/pdf/directional-inserts/60/6300.pdf [entire documentation, especially p. 1, para 5].
PCT Search Reort and Written Opinion; PCT/US 14/24315; Jun. 24, 2014; 15 pages.
Farrow, Emily G., et al.; Iron deficiency drives an autosomal dominant hypophosphatemic rickets (ADHR) phenotype in fibroblast growth factor-23 (Fgf23) knock-in mice; Proceedings of the National Academy of Sciences of the United States; Nov. 15, 2011; pp. E1146-E1155; vol. 108; USA.
Frishberg, Yaacov, et al.; Hyperostosis-Hyperphosphatemia Syndrome: A Congenital Disorder of O-Glycosylation Associated With Augmented Processing of Fibroblast Growth Factor 23; Journal of Bone and Mineral Research; Nov. 13, 2006; pp. 235-242; vol. 22; American Society for Bone and Mineral Research; USA.
Imel, Erik A., et al.; Iron Modifies Plasma FGF23 Differently in Autosomal Dominant Hypophosphatemic Rickets and Healthy Humans; Journal of Clinical Endocrinol Metabolism; Nov. 2011; pp. 3541-3549; 96(11); USA.
Collins, Michael T., et al.; Mechanism of FGF23 processing in Fibrous Dysplasia; Journal of Bone and Mineral Research; Jul. 2, 2011; pp. 1-31; American Society of Bone and Mineral Research; USA.
Shalhoub, Victoria; FGF23 neutralization improves chronic kidney disease-associated hyperparathyroidism yet increases mortality; The Journal of Clinical Investigation; Jul. 2012; pp. 2543-2553; vol. 122 No. 7; USA.
Smith, Edward S., et al.; Biological Variability of Plasma Intact and C-terminal FGF23 Measurements; Journal of Clinical Endocrin Metabolism; Sep. 2012; pp. 1-10; 97(9); The Endocrine Society; USA.

* cited by examiner

*Primary Examiner* — Gary W Counts
(74) *Attorney, Agent, or Firm* — Stetina Brunda Garred & Brucker

(57) ABSTRACT

Immunoassays and methods for detecting and quantifying biological levels of intact fibroblast growth factor (FGF)-23, as well as the N-terminal and C-terminal fragments thereof in a biological sample. The relative amounts or ratios of FGF-23 relative the N-terminal and C-terminal fragments can also be determined. The systems and methods deploy antibodies that are specific to antigenic regions formed upon either the N-terminal or C-terminal regions of FGF-23 and are systematically applied such that intact FGF-23 and the fragments thereof can be detected and quantified. In certain embodiments, dissimilar labels conjugated to tracer antibodies or labeled antibodies specific to N-terminal and/or C-terminal tracer antibodies are utilized to facilitate detection and quantification of both whole length FGF-23 and any fragments thereof.

7 Claims, 20 Drawing Sheets

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
            50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250
```

FIG. 1

```
Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
            35                  40                  45

Leu Met Ile Arg Ser Glu Asp Ala Gly Phe Val Val Ile Thr Gly Val
        50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
        130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
        210                 215                 220

Lys Phe Ile
225
```

FIG. 2

```
Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
                20                  25                  30

Lys Asn Gly His Val Asp Gly Ala Pro His Gln Thr Ile Tyr Ser Ala
            35                  40                  45

Leu Met Ile Arg Ser Glu Asp Ala Gly Phe Val Val Ile Thr Gly Val
        50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg
145                 150                 155
```

FIG. 3

```
Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
                20                  25                  30

Ser Ala Glu Asp Asn Ser Pro Met Ala Ser Asp Pro Leu Gly Val Val
                35                  40                  45

Arg Gly Gly Arg Val Asn Thr His Ala Gly Gly Thr Gly Pro Glu Gly
                50                  55                  60

Cys Arg Pro Phe Ala Lys Phe Ile
65                  70
```

FIG. 4

```
Tyr Pro Asn Ala Ser Pro Leu Leu Gly Ser Ser Trp Gly Gly Leu Ile
1               5                   10                  15

His Leu
```

FIG. 5

```
Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
                20                  25                  30

Lys Asn Gly His Val Asp Gly Ala Pro His Gln Thr Ile
                35                  40                  45
```

FIG. 6

```
Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
            35                  40                  45

Leu Met Ile Arg Ser Glu Asp Ala Gly Phe Val Val Ile Thr Gly Val
        50                  55                  60

Met Ser Arg Arg Tyr Leu Cys Met Asp Phe Arg Gly
65                  70                  75
```

FIG. 7

```
Tyr Pro Asn Ala Ser Pro Leu Leu Gly Ser Ser Trp Gly Gly Leu Ile
1               5                   10                      15

His Leu Tyr Thr Ala Thr Ala Arg Asn Ser Tyr His Leu Gln Ile His
                20                  25                  30

Lys Asn Gly His Val Asp Gly Ala Pro His Gln Thr Ile Tyr Ser Ala
            35                  40                  45

Leu Met Ile Arg Ser Glu Asp Ala Gly Phe Val Val Ile Thr Gly Val
        50                  55                  60

Met Ser Arg Arg Tyr Leu Cys Met Asp Phe Arg Gly Asn Ile Phe Gly
65                  70                  75                      80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
        130                 135                 140

Phe Asn Thr Pro Ile Pro
145             150
```

FIG. 8

```
His Leu Tyr Thr Ala Thr Ala Arg Asn Ser Tyr His Leu Gln Ile His
1               5                   10                      15
```

FIG. 9

```
Tyr His Leu Gln Ile His Lys Asn Gly His Val Asp Gly Ala Pro His
1               5                   10                  15

Gln Thr Ile
```

FIG. 10

```
Asn Gly His Val Asp Gly Ala Pro His Gln Thr Ile Tyr Ser Ala Leu
1               5                   10                  15

Met Ile Arg Ser Glu Asp Ala Gly
            20
```

FIG. 11

```
Pro His Gln Thr Ile Tyr Ser Ala Leu Met Ile Arg Ser Glu Asp Ala
1               5                   10                  15

Gly
```

FIG. 12

```
Tyr Ser Ala Leu Met Ile Arg Ser Glu Asp Ala Gly Phe Val Val Ile
1               5                   10                  15
```

FIG. 13

```
Val Ile Thr Gly Val Met Ser Arg Arg Tyr Leu Cys Met Asp Phe Arg
1               5                   10                  15

Gly
```

FIG. 14

```
Ser Arg Arg Tyr Leu Cys Met Asp Phe Arg Gly Asn Ile Phe Gly Ser
1               5                   10                  15

His Tyr Phe Asp Pro Glu Asn Cys Arg Phe
            20                  25
```

FIG. 15

```
Gly Asn Ile Phe Gly Ser His Tyr Phe Asp Pro Glu Asn Cys Arg Phe
1               5                   10                  15

Gln His Gln Thr Leu
                20
```

FIG. 16

```
Pro Glu Asn Cys Arg Phe Gln His Gln Thr Leu Glu Asn Gly Tyr Asp
1               5                   10                  15

Val Tyr His Ser Pro
                20
```

FIG. 17

```
Thr Leu Glu Asn Gly Tyr Asp Val Tyr His Ser
1               5                   10
```

FIG. 18

```
Pro Gln Tyr His Phe Leu Val Ser Leu Gly Arg Ala Lys Arg Ala Phe
1               5                   10                  15

Leu Pro Gly Met Asn
                20
```

FIG. 19

```
Pro Gln Tyr His Phe Leu Val Ser Leu Gly Arg Ala Lys Arg Ala Phe
1               5                   10                  15

Leu Pro Gly Met Asn
                20
```

FIG. 20

```
Asn Pro Pro Pro Tyr Ser Gln Phe Leu Ser Arg Arg Asn Glu Ile Pro
1               5                   10                  15

Leu Ile His Phe Asn
                20
```

FIG. 21

```
Arg Arg Asn Glu Ile Pro Leu Ile His Phe Asn Thr Pro Ile Pro
1               5                   10                  15
```

FIG. 22

```
Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys
                20                  25
```

FIG. 23

Glu Arg Asp Pro Leu Asn Val Leu Lys Pro Arg Ala Arg Met Thr Pro
1               5                   10                  15

Ala Pro Ala Ser Cys
            20

FIG. 24

Glu Arg Asp Pro Leu Asn Val Leu Lys Pro Arg Ala Arg Met Thr Pro
1               5                   10                  15

Ala Pro Ala Ser Cys Ser Gln Glu Leu Pro Ser Ala Glu Asp Asn Ser
            20                  25                  30

Pro Met Ala Ser Asp Pro Leu Gly Val Val Arg Gly Gly Arg Val Asn
        35                  40                  45

Thr His Ala Gly Gly Thr Gly Pro Glu Gly Cys
        50              55

FIG. 25

Cys Ser Gln Glu Leu Pro Ser Ala Glu Asp Asn Ser Pro Met Ala Ser
1               5                   10                  15

Asp

FIG. 26

```
Cys Ser Gln Glu Leu Pro Ser Ala Glu Asp Asn Ser Pro Met Ala Ser
1               5                   10                  15

Asp Pro Leu Gly Val Val Arg Gly Gly Arg Val Asn Thr His Ala Gly
                20                  25                  30

Gly Thr Gly Pro Glu Gly Cys
            35
```

FIG. 27

```
Gly Val Val Arg Gly Gly Arg Val Asn Thr His Ala Gly Gly Thr Gly
1               5                   10                  15

Pro Glu Gly Cys
            20
```

FIG. 28

```
Gly Val Val Arg Gly Gly Arg Val Asn Thr His Ala Gly Gly Thr Gly
1               5                   10                  15

Pro Glu Gly Cys Arg Pro Phe Ala Lys Phe Ile
            20                  25
```

FIG. 29

```
Gly Arg Val Asn Thr His Ala Gly Gly Thr Gly Pro Glu Gly Cys Arg
1               5                   10                  15

Pro Phe Ala Lys Phe Ile
                20
```

FIG. 30

```
Gly Pro Glu Gly Cys Arg Pro Phe Ala Lys Phe Ile
1               5                   10
```

FIG. 31

IMMUNOASSAYS AND METHODS OF DETECTING AND MEASURING INTACT FIBROBLAST GROWTH FACTOR 23, AND C-TERMINAL AND N-TERMINAL FRAGMENTS THEREOF

CROSS-REFERENCE TO RELATED APPLICATIONS

Not Applicable

STATEMENT RE FEDERALLY SPONSORED RESEARCH/DEVELOPMENT

Not Applicable

BACKGROUND

The present invention is directed to systems and methods for detecting and quantifying whole length or intact Fibroblast Growth Factor (FGF)-23 in a biological sample, as well as detecting and quantifying N-terminal or C-terminal fragments thereof, also present in such sample. The present invention further provides for methods for determining the relative amounts of intact FGF-23 relative to said N-terminal and C-terminal fragments.

FGF-23 is the $22^{nd}$ documented fibroblast growth factor that, in humans, consists of a 251 amino acid protein having the sequence set forth at SEQ ID NO.:1. Among FGF-23's distinguishing features include a 24 amino acid signal peptide in the N-terminal portion and a unique C-terminal structure. Exemplary of the teachings of FGF-23 and its structure and properties are set forth in U.S. Pat. No. 7,223,563, issued May 29, 2007 entitled FIBROBLAST GROWTH FACTOR (FGF-23) NUCLEIC ACIDS, the teachings of which are expressly incorporated herein by reference.

FGF-23 is a major regulator of phosphate homeostasis. In this regard, when excess phosphate is present, the kidneys normally excrete such excess in the urine, and when more phosphate is needed by the body, the kidneys reabsorb the phosphate into the blood stream. With respect to the latter function, FGF-23 signals the kidneys to stop reabsorbing phosphate into the blood stream. Research has further suggested that FGF-23 helps determine how much phosphate from a person's diet is absorbed by the intestines and further plays a role in regulating the formation of biologically active Vitamin D analogs.

FGF-23 is primarily secreted by bone, followed by the thymus, heart and brain. Low levels are also secreted by other tissues. In order to function, FGF-23 must be secreted from the cells and must bind to a receptor protein. In order to be secreted, FGF-23 must be glycosylated whereby sugar molecules are attached to FGF-23 via a protein, namely, ppGalNacT3. As understood, such glycosylation allows FGF-23 to move out of the producing cell and further protects the FGF-23 molecule from being degraded. Once outside of the secreting cell, FGF-23 binds to the FGF-23 receptor protein that spans the membrane of the kidney cells whereby binding of FGF-23 to such receptor stimulates signaling that stops phosphate reabsorption by the kidneys into the blood stream.

Importantly, only "intact" FGF-23 is considered bioactive in regards to its role in phosphate regulation. In this regard, it is well understood that the first 24 amino acids of the N-terminal of FGF-23 consists of a signal peptide and that the secreted, bioactive form of FGF-23 is understood to consist of 227 amino acids extending from the $25^{th}$ amino acid residue to the $251^{st}$, as set forth at SEQ ID NO.: 2. Moreover, FGF-23 is cleaved between amino acid positions 179-180, which consequently inactivates the protein and produces both an N-terminal fragment consisting of amino acids 25-179 (SEQ ID NO.: 3) and a C-terminal fragment consisting of amino acids 180-251 (SEQ ID NO.: 4). Such cleavage is understood to facilitate and regulate the amount of active FGF-23 circulating in the blood stream. Moreover, by means of a feedback loop, falling serum phosphate levels lead to diminished FGF-23 secretion thus further decreasing phosphate reabsorption.

Measurement of serum FGF-23 can assist in the diagnosis and management of disorders of phosphate and bone metabolism in patients with either normal or impaired renal function. In this respect, over-activity of FGF-23 reduces phosphate reabsorption by the kidneys, leading to low levels of phosphate in the blood (i.e., hypophosphatemia). Such conditions can cause problems with bone growth and strength, as occurs in people afflicted with autosomal dominant hypophosphatemic rickets (ADHR) and other phosphate-wasting disorders such as X-linked and autosomal recessive hypo-phosphotemia. A shortage of available FGF-23, on the other hand, decreases the signaling function of FGF-23 and consequently increases the amount of phosphate that is reabsorbed back into the blood stream by the kidneys, leading to hyperphosphatemia, which can result in calcinosis whereby excess phosphate combines with calcium to form deposits that build up in soft tissues.

Given the clinical importance of determining the presence and quantity of FGF-23, commercial immunoassays have been developed that are operative to detect and quantify the presence of FGF-23. Exemplary of such products include the Human Intact FGF-23 ELISA Kit produced by Immutopics, Inc. of San Clemente, Calif., which are disclosed and claimed in U.S. Pat. No. 7,094,551 entitled IMMUNOASSAYS, ASSAY METHODS, ANTIBODIES AND METHOD FOR CREATING ANTIBODIES FOR DETECTING FGF-23, issued on Aug. 22, 2006, the teachings of which are expressly incorporated herein by reference. Likewise, commercial immunoassays are available for detecting the intact as well as post-cleavage C-terminal fragments of FGF-23, which include the Human FGF-23 (C-Term) ELISA Kit, also produced by Immutopics, Inc. of San Clemente, Calif. With respect to the latter, the same is operative to detect the carboxyl-terminal portion of FGF-23, namely, amino acids 180-251 produced following cleavage of the whole length FGF-23 molecule, as discussed above.

Despite the importance of measuring serum FGF-23 and, in certain cases, the cleaved fragments thereof, substantial shortcomings exist with respect to the ability to not only detect the relative amounts of intact serum FGF-23 and the cleaved fragments thereof, but the relative amounts or ratios of intact FGF-23 as compared to its inactive cleaved fragments. In this regard, there are a number of specific conditions where the relative amounts of intact FGF-23 and the inactive fragments of FGF-23, and in particular the C-terminal fragments of FGF-23, have profound clinical implications. For example, in rare genetic disorders, such as mutations in GALNT3 that prevent normal glycosylation of FGF-23, only very little biologically active intact FGF-23 is secreted by osteocytes or other FGF-23 producing cells, thus often leading to severe hyperphosphatemia and consequently vascular calcifications. These patients have little or no intact FGF-23 in the circulation, but often very high levels of C-terminal FGF-23 fragments.

Similarly, patients with the McCune-Albright syndrome (activating Gs-alpha mutation) can have elevated intact FGF- 23 levels leading to increased urinary phosphate excretion. However, the levels of C-terminal FGF-23 fragments are more significantly elevated than the levels of intact FGF-23, especially in those patients who have hypophosphatemia due to mosaic expression of a constitutively active Gs-alpha in bone, which consequently leads to a bigger FGF-23 C-terminal fragment to intact FGF-23 ratio.

Still further, research has indicated a link between the effect of dietary iron levels and the relative amounts of intact FGF-23 and the C-terminal fragments thereof. In one recently published study, wild-type mice on a low iron diet express FGF-23 mRNA very abundantly in bone, and these animals demonstrated a major increase in C-terminal FGF23 fragments levels, but not intact FGF-23, and they consequently did not become hypophosphatemic. Data consistent with these rodent data seem to likewise exist for healthy humans, in whom it was shown that iron levels correlate with C-terminal fragment FGF-23 levels but not with intact FGF-23 levels. In contrast, ADHR patients with an FGF-23 mutation that impairs cleavage at the RXXR site between amino acids 176 and 179, were shown to have a good correlation between iron levels and intact FGF-23 or C-terminal FGF-23 fragment levels. Furthermore, another study has shown that ferritin levels correlate with C-terminal FGF-23 fragments, but not with intact FGF-23 levels. Heavy blood losses in humans and the resulting iron deficiency therefrom, also appear to correlate with elevated C-terminal fragments of FGF-23, but not intact FGF-23 levels.

As another example, patients with earlier chronic kidney disease (CKD) stages have levels of C-terminal FGF-23 fragments that are often equally elevated as intact FGF-23 levels. As these patients approach end state renal disease (ESRD), intact FGF-23 is the predominant form of FGF-23 in the circulation. The intact FGF-23 appears to be the form of FGF-23 that has "off-target" effects resulting in poor outcome (i.e., increased mortality and accelerated loss of renal function in CKD).

As such, monitoring the amount and appearance of both intact FGF-23 in addition to the C-terminal fragments of FGF-23, as well as the relative amounts of one another, would be of considerable diagnostic importance. Indeed, the need for systems and methods to effectively monitor both the presence of intact FGF-23 and the C-terminal fragments thereof, including their relative amounts to one another, would be exceptionally useful in not only monitoring a variety of specific disease states, impaired renal function and other conditions, but for also monitoring the effectiveness of potential therapeutic agents that seek to modulate FGF-23 activity. With respect to the latter, it is conceivable that therapeutics could be developed that increase or decrease the amount of intact FGF-23 in circulation, as opposed to the cleaved inactive fragments thereof. In this regard, any type of therapeutic that is operative to accelerate the cleavage of intact FGF-23 could be beneficial for the treatment of patients with FGF-23 dependent hypophosphatemia, such as X-linked hypophosphatemia (XLH) or autosomal recessive hypophosphatemia (ARHP). Likewise, accelerated FGF-23 cleavage would be of considerable importance for patients with chronic kidney disease or end stage renal disease, who have tremendous FGF-23 elevations that are strongly expected in contributing to cardiac hypertrophy and to kidney disease progressions.

Accordingly, there is a substantial need in the art for immunoassays and methods that can serve such diagnostic needs and potential applications. There is a further need in the art for such systems and methods that are highly accurate, can be readily deployed utilizing known, existing immunoassay technology, are exceptionally effective and efficient, and are operative to provide diagnostic information, particularly with respect to ratios and relative amounts of intact FGF-23 versus fragments thereof that have not heretofore been available.

BRIEF SUMMARY

The present invention specifically addresses and alleviates the above-identified deficiencies in the art. In this regard, the present invention is directed to immunoassay systems and methods for detecting both whole length FGF-23 and the cleaved C-terminal fragments and N-terminal fragments thereof in a given sample, as well as their respective amounts relative one another. Such immunoassay systems and methods are thus operative to provide relative percentages or ratios of intact FGF-23 versus the C-terminal and N-terminal fragments thereof, which are thus useful in detecting and monitoring a variety of conditions, such as ESRD, CKD, and other genetic disorders associated with FGF-23 mediated processes. The immunoassay systems and methods of the present invention will also be extremely useful in monitoring the activity and potential therapeutic activity of one or more therapeutic agents designed to regulate FGF-23 function, including but not limited to therapeutic agents for regulating the catabolic processes operative to cleave intact FGF-23 into inactive fragments.

To achieve that end, the immunoassay systems and methods of the present invention deploy antibodies having select specificity to antigenic regions of either the N-terminal portion of FGF-23 or the C-terminal portion of FGF-23. The specific antigenic regions of the N-terminal and C-terminal portions of FGF-23 to which the antibodies may have an affinity for and to which the antibodies may specifically bind are set forth in U.S. Pat. No. 7,094,551 entitled IMMUNOASSAYS, ASSAY METHODS, ANTIBODIES AND METHOD FOR CREATING ANTIBODIES FOR DETECTING FGF-23, issued on Aug. 22, 2006, the teachings of which are expressly incorporated herein by reference. Per the teachings of such patent, there are provided combinations of N-terminal and C-terminal antibodies that are operative to cooperate to measure only bioactive, intact FGF-23 via conventional immunometric or sandwich-type assay design.

The present invention, in contrast, builds upon such existing technology by utilizing antibodies specific to epitopes formed on either the N-terminal or C-terminal of FGF-23 that are operative to detect and quantify both the presence of intact FGF-23 and the N-terminal and C-terminal fragments thereof via a conventional immunometric or sandwich-type assay. Such objective is accomplished by a first antibody that is specific for antigenic regions on either the C-terminal region of FGF-23 (i.e., amino acids 180-251) or the N-terminal region of FGF-23 (i.e., amino acids 25-179 of FGF-23) that is operative to bind both intact FGF-23 and either the N-terminal or C-terminal fragments thereof to which the capture antibodies will specifically bind.

Such first antibody may be a bound capture antibody or, alternatively, may be a conjugated antibody that is initially maintained in solution. The detection and quantification of intact FGF-23 and the fragments thereof are then capable of being determined by the application of a separately labeled second N-terminal and C-terminal tracer antibodies, which may be introduced sequentially or simultaneously with the first antibody. Such second antibody may use dissimilar labels conjugated thereto, including indirect detection through a secondary antibody. In this regard, the degree of binding by the N-terminal tracer antibody may be provided by a first modality and the degree of the C-terminal antibody binding is provided by a different modality.

It is contemplated that any conventional labels and combination of labels may be deployed in the practice of the present invention, including but not limited to biotinylation, radioisotopes, fluorophores and enzymes that are conjugated to the tracer antibodies. Moreover, it is contemplated that the present invention can utilize indirect detection of either the N-terminal or C-terminal tracer antibodies via labeled secondary antibodies specific for those respective tracer antibodies, as is known and extensively practiced in the art.

In use, it is contemplated that the immunoassay systems disclosed herein may take the form of several general formats. In the first format, a bound N-terminal capture antibody is provided to which is subjected a fluid sample suspected of containing intact FGF-23 and fragments thereof. Per conventional immunometric assay design, any intact FGF-23 molecules or N-terminal fragments thereof will be bound thereby. Any C-terminal fragments that are present will be removed by a subsequent wash step.

Thereafter, a labeled N-terminal tracer antibody is added to thus detect the presence of both the intact FGF-23 and N-terminal fragments thereof that are bound to the N-terminal capture antibody. Next, a labeled C-terminal tracer antibody is added that will thus be operative to bind to the C-terminal of any bound intact FGF-23, and will consequently produce a signal corresponding to the presence and quantity of the C-terminal portion of the intact FGF-23. Such signal is thus indicative of only the intact FGF-23 bound by the assay. In addition to or separate from the sequential application of the N-terminal and C-terminal tracer antibodies and measurement of the respective levels of detection produced thereby, the N-terminal and C-terminal tracer antibodies, respectively, may be conjugated with dissimilar labeling modalities so that the degree of binding by the N-terminal tracer antibody is detected and quantified by a first type of label, such as a fluorophore and the degree of C-terminal binding via a second label, such as a different fluorophore.

To measure the relative amounts of intact FGF-23 and the fragments thereof according to such format, it will be understood that the signal provided by the C-terminal tracer antibody will be indicative of total amount of intact FGF-23 detected by the immunoassay. The signal produced by the label conjugated to the N-terminal tracer antibody, on the other hand, will be indicative of the combined presence of both intact FGF-23 and the N-terminal fragments thereof. Deducting the quantity measured by the C-terminal tracer antibody from the quantity measured by the N-terminal tracer antibody will thus identify the quantity of N-terminal fragments present in such sample. Moreover, in certain applications (which may be dependent on factors such as half-life of FGF-23 fragments in circulation, further enzymatic degradation and excretion by the kidneys), cleavage of intact FGF-23 may produce equimolar amounts of N-terminal and C-terminal fragments, and in such cases the amount of C-terminal fragments can also be determined.

The second general immunoassay format is substantially similar to the first format except that a C-terminal capture antibody is provided that is operative to bind with any intact FGF-23 molecules and/or C-terminal fragments thereof present in a sample being tested. Following a wash step, a labeled C-terminal tracer antibody is then provided operative to bind to any intact FGF-23 or C-terminal fragments thereof that are bound to the capture antibody, and is thus operative to indicate the presence and degree of both intact FGF-23 and C-terminal fragments present in the sample. A labeled N-terminal tracer antibody is then provided that will thus be operative to bind to the N-terminal portion of intact FGF-23 and thus produce a signal corresponding to the presence and degree of only the intact FGF-23. By sequentially measuring the signal produced firstly by the C-terminal tracer antibody followed by measuring the signal produced by the N-terminal tracer antibody, the degree of C-terminal fragments and intact FGF-23 can be readily ascertained. Also, as discussed above, the C-terminal and N-terminal tracer antibodies may have dissimilar detection modalities that can separately correspond to the degree of C-terminal fragments and intact FGF-23 that is present in the sample.

In a third immunoassay format, a mixture of both N-terminal and C-terminal capture antibodies are provided that are bound and operative to bind with any intact FGF-23 molecules or any N-terminal or C-terminal fragments thereof, respectively. In this regard, the N-terminal capture antibodies will be operative to bind both intact FGF-23 and N-terminal fragments thereof whereas the C-terminal capture antibodies will bind with both intact FGF-23 and C-terminal fragments thereof. The entirety of the bound C-terminal and N-terminal capture antibodies may also be distributed in selective amounts as may be desired for a particular test or application.

Thereafter, a respective one of the tracer antibodies, such as a labeled C-terminal tracer antibody is added, which will thus bind to and detect the presence of any intact FGF-23 or C-terminal fragments thereof bound to the C-terminal capture antibody, which can be measured and quantified. The respective other tracer antibody, namely, the labeled N-terminal tracer antibody, is then added that will likewise bind to any intact FGF-23 or N-terminal fragments that are bound to the N-terminal capture antibody, and thus produce a signal corresponding thereto. By sequentially measuring the degree and intensity of the signaling produced by the labeled tracer antibodies, the presence and quantity of intact FGF-23, as well as the N-terminal and C-terminal fragments thereof can be readily determined (as may be accomplished by comparison against known samples and the like). As per the other aforementioned formats, in addition to or separate from the sequential addition of the sequential application of the C-terminal and N-terminal tracer antibodies, such tracer antibodies may be provided with dissimilar labeling modalities which are thus operative to indicate the respective degree of either N-terminal or C-terminal binding by the respective tracer antibodies.

The relative degree of either N-terminal or C-terminal fragments versus intact FGF-23 can be readily determined using known immunoassay principles well-recognized in the art. For example, in the first immunoassay format of the present invention, a strong level of detection by the N-terminal tracer antibody without a correspondingly strong signal produced by the C-terminal tracer antibody is thus indicative that N-terminal fragments are present and the relative strength of the N-terminal tracer antibody relative the C-terminal tracer antibody is operative to determine the relative amounts of fragments versus intact FGF-23. Similarly, with respect to the second format, strong signaling by the C-terminal tracer antibody without a corresponding strength in signal in the N-terminal tracer antibody is indicative of C-terminal fragments relative to intact FGF-23. In both the first and second formats, equal signaling by the N-terminal and C-terminal tracer antibodies is thus indicative of presence of intact FGF-23.

Likewise, with respect to the third format of the immunoassay of the present invention, relative signaling of the respective C-terminal and N-terminal tracer antibodies correspond to the relative amounts of N-terminal and C-terminal fragments of FGF-23 in relation to the amount of intact FGF-23 whereas signaling by the tracer antibodies to a degree equivalent to the respective amounts of N-terminal and C-terminal capture antibodies is indicative of intact FGF-23. In this regard, both N-terminal and C-terminal tracer antibodies will bind to each intact FGF-molecule captured whereas only one such tracer antibody will bind to the extent only a fragment of FGF-23 is bound to a capture antibody. The differential in signal strength, as may be compared against a standardized curve, can thus be used to determine the relative amounts of both intact FGF-23 and its fragments.

As an alternative to the aforementioned formats utilizing the combination of bound capture antibodies and C-terminal and N-terminal tracer antibodies, it is believed that such antibodies may be utilized in a solution format whereby all of the antibodies, including the aforementioned "capture" antibodies are in solution. In such embodiment, all of the antibodies, namely, the first "capture" antibodies and second "tracer" N-terminal and C-terminal antibodies, will be introduced simultaneously with each respective antibody being operative to be separately detected through any of the aforementioned varieties of antibody detection. Along these lines, it is contemplated that the use of biotin/avidin binding characteristics or the indirect detection of the antibodies, namely, detection through the use of secondary antibodies specific for either the "capture" or "tracer" antibodies will be exceptionally effective in such applications.

In all cases, the immunoassay systems and methods of the present invention are thus operative to ultimately provide an indication as to the degree of fragments of FGF-23 relative to intact FGF-23 present in a sample. This data may be indicative of certain types of disease states and further may be operative to measure the catabolic activity whereby intact FGF-23 is cleaved into inactive fragments. Along those lines, numerous modifications and additions utilizing existing immunoassay technology may be readily envisioned and incorporated in the practice of the present invention to further those ends.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 illustrates the 251 amino acid sequence of human FGF-23 (SEQ ID NO.: 1)

FIG. 2 illustrates an amino acid sequence corresponding to amino acid residues 25-251 of human FGF-23 (SEQ ID No.: 2)

FIG. 3 illustrates an amino acid sequence corresponding to amino acid residues 25-179 of human FGF-23 (SEQ ID NO.: 3)

FIG. 4 illustrates an amino acid sequence corresponding to amino acid residues 180-251 of human FGF-23 (SEQ ID NO.: 4)

FIG. 5 illustrates an amino acid sequence corresponding to amino acid residues 25-42 of human FGF-23 (SEQ ID NO.: 5).

FIG. 6 illustrates an amino acid sequence corresponding to amino acid residues 25-69 of human FGF-23 (SEQ ID NO.: 6).

FIG. 7 illustrates an amino acid sequence corresponding to amino acid residues 25-100 of human FGF-23 (SEQ ID NO.: 7).

FIG. 8 illustrates an amino acid sequence corresponding to amino acid residues 25-174 of human FGF-23 (SEQ ID NO.: 8).

FIG. 9 illustrates an amino acid sequence corresponding to amino acid residues 41-56 of human FGF-23 (SEQ ID NO.: 9).

FIG. 10 illustrates an amino acid sequence corresponding to amino acid residues 51-69 of human FGF-23 (SEQ ID NO.: 10).

FIG. 11 illustrates an amino acid sequence corresponding to amino acid residues 58-81 of human FGF-23 (SEQ ID NO.: 11).

FIG. 12 illustrates an amino acid sequence corresponding to amino acid residues 65-81 of human FGF-23 (SEQ ID NO.: 12).

FIG. 13 illustrates an amino acid sequence corresponding to amino acid residues 70-85 of human FGF-23 (SEQ ID NO.: 13).

FIG. 14 illustrates an amino acid sequence corresponding to amino acid residues 84-100 of human FGF-23 (SEQ ID NO.: 14).

FIG. 15 illustrates an amino acid sequence corresponding to amino acid residues 90-115 of human FGF-23 (SEQ ID NO.: 15).

FIG. 16 illustrates an amino acid sequence corresponding to amino acid residues 100-120 of human FGF-23 (SEQ ID NO.: 16).

FIG. 17 illustrates an amino acid sequence corresponding to amino acid residues 110-130 of human FGF-23 (SEQ ID NO.: 17).

FIG. 18 illustrates an amino acid sequence corresponding to amino acid residues 119-129 of human FGF-23 (SEQ ID NO.: 18).

FIG. 19 illustrates an amino acid sequence corresponding to amino acid residues 130-150 of human FGF-23 (SEQ ID NO.: 19).

FIG. 20 illustrates an amino acid sequence corresponding to amino acid residues 140-160 of human FGF-23 (SEQ ID NO.: 20).

FIG. 21 illustrates an amino acid sequence corresponding to amino acid residues 150-170 of human FGF-23 (SEQ ID NO.: 21).

FIG. 22 illustrates an amino acid sequence corresponding to amino acid residues 160-174 of human FGF-23 (SEQ ID NO.: 22).

FIG. 23 illustrates an amino acid sequence corresponding to amino acid residues 180-206 of human FGF-23 (SEQ ID NO.: 23).

FIG. 24 illustrates an amino acid sequence corresponding to amino acid residues 186-206 of human FGF-23 (SEQ ID NO.: 24).

FIG. 25 illustrates an amino acid sequence corresponding to amino acid residues 186-244 of human FGF-23 (SEQ ID NO.: 25).

FIG. 26 illustrates an amino acid sequence corresponding to amino acid residues 206-222 of human FGF-23 (SEQ ID NO.: 26).

FIG. 27 illustrates an amino acid sequence corresponding to amino acid residues 206-244 of human FGF-23 (SEQ ID NO.: 27).

FIG. 28 illustrates an amino acid sequence corresponding to amino acid residues 225-244 of human FGF-23 (SEQ ID NO.: 28).

FIG. 29 illustrates an amino acid sequence corresponding to amino acid residues 225-251 of human FGF-23 (SEQ ID NO.: 29).

FIG. 30 illustrates an amino acid sequence corresponding to amino acid residues 230-251 of human FGF-23 (SEQ ID NO.: 30).

FIG. 31 illustrates an amino acid sequence corresponding to amino acid residues 240-251 of human FGF-23 (SEQ ID NO.: 31).

DETAILED DESCRIPTION

Figure 32:
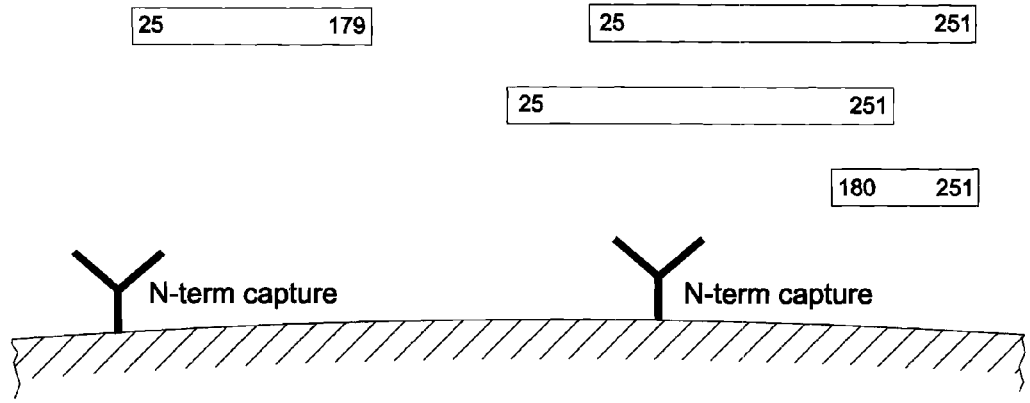
FIG. 32 is a side view of an immunoassay incorporating bound antibodies specific for an antigenic region formed upon an N-terminal region of FGF-23 as confined within amino acids 25-179 of FGF-23 (SEQ ID NO.: 3) wherein said antibodies operative to bind to intact FGF-23 and N-terminal fragments of FGF-23 present in a sample.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

The present invention encompasses immunoassay systems and methods that are designed to detect, in a serum sample, the presence and quantity of both intact FGF-23, as well as C-terminal and N-terminal fragments of FGF-23, which in turn enables the relative amounts or ratios of intact FGF-23 to the fragments thereof to be readily determined.

For purposes of the present invention, the term "intact FGF-23" refers to a polypeptide comprising the amino acid sequence set forth in either FIG. 1, SEQ ID NO.: 1 or FIG. 2, SEQ ID NO.: 2. In this regard, intact FGF-23 as referred to herein is meant to encompass those forms of FGF-23 that possess or are capable of possessing biological activity, which as will be understood by those skilled in the art as having at least the sequence of the polypeptide of SEQ ID NO.: 2, namely, the sequence of amino acid residues 25-251.

Similarly, the term "N-terminal FGF-23 fragment" will mean those segments of the N-terminal of FGF-23 following cleavage of intact FGF-23, which will comprise the sequence of amino acid residues 25-179 of FGF-23 (SEQ ID NO. 3). Such N-terminal FGF-23 fragments will also define discrete antigenic sequences of amino acids to which certain antibodies, as utilized in the immunoassays disclosed herein, will have an affinity for and to which they will specifically bind. Those antigenic sequences of the N-terminal of FGF-23 include amino acid residues 25-42 of FGF-23 (SEQ ID NO. 5); amino acid residues 25-69 of FGF-23 (SEQ ID NO. 6); amino acid residues 25-100 of FGF-23 (SEQ ID NO. 7); amino acid residues 25-174 of FGF-23 (SEQ ID NO. 8); amino acid residues 41-56 of FGF-23 (SEQ ID NO. 9); amino acid residues 51-69 of FGF-23 (SEQ ID NO. 10); amino acid residues 58-81 of FGF-23 (SEQ ID NO. 11); amino acid residues 65-81 of FGF-23 (SEQ ID NO. 12); amino acid residues 70-85 of FGF-23 (SEQ ID NO. 13); amino acid residues 84-100 of FGF-23 (SEQ ID NO. 14); amino acid residues 90-115 of FGF-23 (SEQ ID NO. 15); amino acid residues 100-120 of FGF-23 (SEQ ID NO. 16); amino acid residues 110-130 of FGF-23 (SEQ ID NO. 17); amino acid residues 119-129 of FGF-23 (SEQ ID NO. 18); amino acid residues 130-150 of FGF-23 (SEQ ID NO. 19); amino acid residues 140-160 of FGF-23 (SEQ ID NO. 20); amino acid residues 150-170 of FGF-23 (SEQ ID NO. 21); and amino acid residues 160-174 of FGF-23 (SEQ ID NO. 22).

Conversely, the term "C-terminal FGF-23 fragment" will mean those segments of the C-terminal of FGF-23 following cleavage of intact FGF-23, which will comprise the sequence of amino acid residues 180-251 of FGF-23 (SEQ ID NO. 4). Likewise, these C-terminal FGF-23 fragments will define discrete antigenic sequences of amino acids to which certain antibodies will possess an affinity for and to which those antibodies will specifically bind. Those C-terminal antigenic sequences include amino acid residues 180-206 of FGF-23 (SEQ ID NO. 23); amino acid residues 186-206 of FGF-23 (SEQ ID NO. 24); amino acid residues 186-244 of FGF-23 (SEQ ID NO. 25); amino acid residues 206-222 of FGF-23 (SEQ ID NO. 26); amino acid residues 206-244 of FGF-23 (SEQ ID NO. 27); amino acid residues 225-244 of FGF-23 (SEQ ID NO. 28); amino acid residues 225-251 of FGF-23 (SEQ ID NO. 29); amino acid residues 230-251 of FGF-23 (SEQ ID NO. 30); and amino acid residues 240-251 of FGF-23 (SEQ ID NO. 31) of the intact FGF-23 molecule.

Also, for certain antibodies disclosed above, it is contemplated that some antigenic regions to which the antibodies specifically bind may have amino acids that are glycosylated, as occurs in naturally-occurring FGF-23, and that the antibodies will be operative to bind to such antigenic structure.

For purposes of practicing the present invention, it will be readily understood by those skilled in the art that antibodies will be derived that will have an affinity for and will specifically bind to discrete antigenic regions formed on either the N-terminal or the C-terminal of FGF-23. Along those lines, such antibodies may be derived to the aforementioned antigenic regions formed on either the N-terminal or C-terminal amino acid portions of FGF-23 per conventional practices well-known and readily understood in the art. In particular, antibodies to the aforementioned antigenic regions may be derived pursuant to the teachings of U.S. Pat. No. 7,094,551, entitled IMMUNOASSAYS, ASSAY METHODS, ANTIBODIES AND METHOD FOR CREATING ANTIBODIES FOR DETECTING FGF-23, issued on Aug. 22, 2006, the teachings of which are expressly incorporated by reference. In this regard, it is expressly contemplated that the antibodies that will specifically bind to the specified antigenic regions of the N-terminal and C-terminal of FGF-23 may be either polyclonal or monoclonal, as previously taught by Applicants.

It is likewise contemplated that conventional labels may be utilized that are conjugated to certain of the antibodies referenced herein, referred to as tracer antibodies, that are operative to detect the presence of either intact FGF-23 and/or N-terminal and C-terminal fragments thereof, as discussed more fully below. In this regard, the present invention expressly contemplates the use of any detectable moiety known in the art, including but not limited to, radioactive, fluorescent, enzymatic and/or dye-type tracers that can be conjugated to an antibody to thus enable the antibody to serve as tracer or detection antibody as will be readily understood by those skilled in the art. For example, such label may comprise biotin to which horseradish peroxidase (HRP) conjugated to avidin will bind for subsequent detection. In such applications that are well understood by those skilled in the art, the enzymatic activity of the antibody bound to the target antigenic epitope can operatively be measured utilizing conventional methods, such as through spectrophotometric analysis as compared to a standardized reference.

It is likewise contemplated that dissimilar types of labels may be utilized, also discussed in greater length below, whereby a label for an N-terminal tracer antibody will be dissimilar to a label utilized in connection with a C-terminal tracer antibody. In such applications, two dissimilar signals will thus be produced that are indicative of the respective tracer antibody binding to discrete and separate antigenic sequences formed on the N-terminal and C-terminal portions of the FGF-23 molecule.

Still further, it is contemplated that the aforementioned antibodies having specificity to antigenic regions of the N-terminal and C-terminal portions of the FGF-23 molecule may be measured indirectly via a labeled second antibody that is specific to a particular tracer antibody binding to a target antigenic region of either the N-terminal or C-terminal of FGF-23. Such secondary antibodies and their use in an indirect immunoassay application is likewise well-known in the art and readily capable of being practiced in connection with the immunoassays of the present invention.

Given the aforementioned array of the various types of antibodies that can be derived that are specific to discrete antigenic regions of either the N-terminal or C-terminal amino sequences of FGF-23, and the conventional labeling that can be conjugated therewith, the same can thus be configured in the novel manner devised by Applicants to measure not only intact FGF-23, but the N-terminal and/or C-terminal fragments thereof, as well as the amount of intact FGF-23 relative to said fragments in a given sample. To that end, the present invention expressly envisions at least three general immunoassay configurations that are operative to selectively detect, quantify and compare the relative amounts of intact FGF-23 and the fragments thereof in a given sample.

Referring now to FIGS. 32-35, there is illustrated the components and sequential steps of performing an immunoassay per a preferred embodiment of the present invention. Referring initially to FIG. 32, there is provided a capture antibody having an affinity for and operative to specifically bind to an amino acid sequence formed upon the N-terminal region of FGF-23 (i.e., amino acids 25-179, SEQ ID NO.: 3). Such antibody may be derived to have a specificity to any of the antigenic regions discussed above with respect to the N-terminal of the FGF-23 molecule. As will be appreciated by those skilled in the art, the specificity to which the antibody will specifically bind will be selectively chosen so as to minimize steric hindrance and allow for the binding of additional antibodies to other distinct regions on the FGF-23 molecule. As discussed above, such antibodies may be produced by any of a variety of well-known and commercial means, and may include either polyclonal or monoclonal antibodies.

Figure 33:
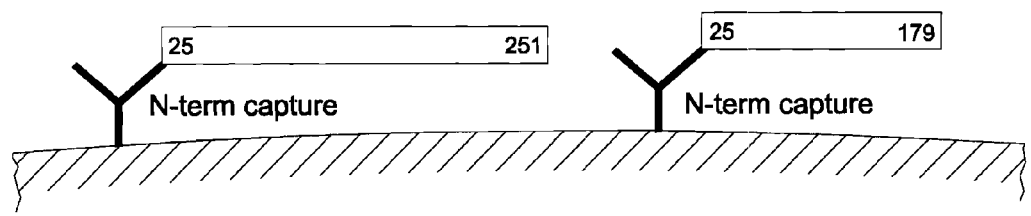
FIG. 33 is a side view of the assay of FIG. 32 depicting molecules of intact FGF-23 and N-terminal fragments thereof binding to the immobilized capture antibody.

To detect the target peptides, a test sample containing both intact FGF-23, represented by the block sequence 25-251, as well as fragments thereof, including N-terminal fragments represented by the block 25-179 are contacted with the N-terminal capture antibodies, as shown in FIG. 33. Due to the affinity of the N-terminal capture antibody to those antigenic regions formed on the N-terminal region of FGF-23, the N-terminal capture antibody is thus operative to bind both intact FGF-23 and the N-terminal fragments thereof, as illustrated. As will be understood, those fragments of FGF-23 that do not contain the antigenic sequence formed upon the N-terminal region of FGF-23, will thus not bind to the N-terminal capture antibody. This will include any C-terminal fragments of FGF-23. Such non-bound fragments will subsequently be removed via conventional washing step, as will be understood by those skilled in the art.

Figure 34:
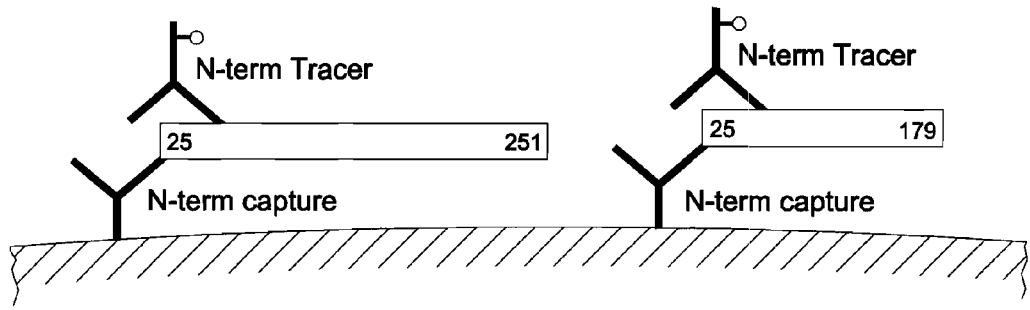
FIG. 34 is a side view of the assay depicted in FIGS. 32 and 33 showing a first tracer antibody having a label affixed thereto, said tracer antibody having an affinity for an antigenic region formed within amino acids 25-179 of FGF-23 (SEQ ID NO.: 3).

To detect the presence of both the intact FGF-23 and N-terminal fragments thereof that are bound to the N-terminal capture antibody, an N-terminal tracer antibody having a label conjugated therewith is introduced to the assay, as shown in FIG. 34, that will be operative to bind to a second antigenic region formed upon the N-terminal region of FGF-23. As will be readily appreciated by those skilled in the art, the specificity for the N-terminal tracer antibody will be dissimilar from that of the N-terminal capture antibody. Along those lines, it will be understood by those skilled in the art that the N-terminal tracer antibody will have a specificity that is not only dissimilar from that of the N-terminal capture antibody, but will further have an affinity for a sequence that will not be sterically hindered, or designed to minimize steric hindrance from the N-terminal capture antibody. In both cases, however, it will be understood that both the capture and tracer N-terminal antibodies will be able to co-bind to the N-terminal region of FGF-23, namely, amino acids 25-179.

As will further be appreciated by those skilled in the art, the label conjugated to the N-terminal tracer antibody will be operative to produce a signal indicative of the presence of both intact FGF-23 and N-terminal fragments thereof that are bound to the N-terminal capture antibody. Such detection and quantification of the intact and N-terminal fragments of FGF-23 may be determined by any of a wide variety of techniques known in the immunoassay arts. Along those lines, the presence and degree of both intact FGF-23 and N-terminal fragments thereof may be determined by conventional methods associated with the particular label utilized such as through radioisotope measurement, enzymatic activity, fluorescence, and the like, as may be determined by any of a variety of conventional analysis means, such as flow cytometry and the like.

Figure 35:
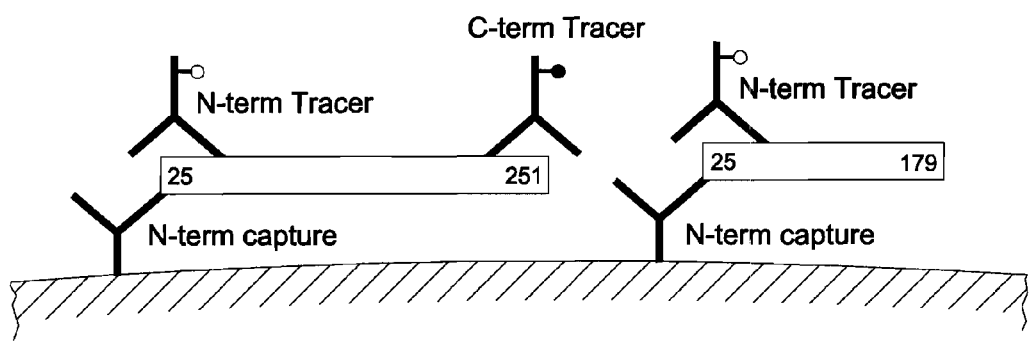
FIG. 35 is a side view of the assay depicted in FIGS. 32-34 showing a second tracer antibody having a label affixed thereto, said second tracer antibody having an affinity for an antigenic region formed within amino acids 180-251 of FGF-23 (SEQ ID NO.: 4).

As a consequence, measurement may thus be readily made of both the intact FGF-23 and the N-terminal fragments thereof in the sample. In order to determine the presence of just the intact FGF-23 present in the sample, there is shown in FIG. 35 the introduction of a C-terminal tracer antibody that is operative to bind to the C-terminal region of FGF-23. According to a preferred embodiment, the C-terminal tracer antibody will be specific for either amino acids 186-206 or 225-244. Other antibodies specific for the antigenic regions discussed above with respect to the C-terminal of FGF-23 may also be suitable. As will be readily understood by those skilled in the art, the specificity for the C-terminal tracer antibody will be selectively determined so as to mitigate steric hindrance from the N-terminal capture and N-terminal tracer antibodies to thus insure as accurate a reading as possible.

As per the N-terminal tracer antibody, the label conjugated to the C-terminal tracer antibody will be operative to provide a signal corresponding to the presence and degree of binding of the C-terminal tracer antibody to the C-terminal region of FGF-23 to which the C-terminal tracer antibody will bind. Such label, as discussed above, may take any of a variety of those known in the art and operative to produce a signal corresponding to the degree of binding by the C-terminal tracer antibody.

The label affixed to the C-terminal tracer antibody may be the same as the tracer utilized in connection with the N-terminal tracer antibody, and measured to determine the degree and strength of the signaling produced thereby. By assessing the corresponding signal produced by the label of the C-terminal tracer antibody, there is thus provided a separate and distinct measurement of only the intact FGF-23 that is bound by the N-terminal capture antibody. Accordingly, by sequentially measuring both the combination of intact FGF-23 and the N-terminal fragments thereof, followed by the measurement of only the intact FGF-23, as measured by the C-terminal tracer antibody, two measurements may be derived that are operative to indicate both the degree of N-terminal fragments, as determined by the signaling activity provided by the N-terminal tracer antibody minus the activity of the C-terminal tracer antibody, and only the intact FGF-23, as measured solely by the C-terminal tracer antibody activity.

In order to more specifically measure these discrete components, namely the labeling activity of the N-terminal tracer antibody and the C-terminal tracer antibody, it is contemplated that dissimilar labels can be used in combination with each respective tracer antibody. For example, the label utilized with the N-terminal tracer antibody may take the form of a radioisotope label (e.g. $Co^{57}$ or $I^{125}$) or two different fluorophores. By utilizing dissimilar labels, discrete measurements can be made of both the degree of binding by each respective tracer antibody. Moreover, by comparing the labeling activity to known standards and calibrated findings, it is contemplated that the use of dissimilar tracers can independently verify the respective degree of binding occurring by the N-terminal and C-terminal tracer antibodies.

Figure 36:
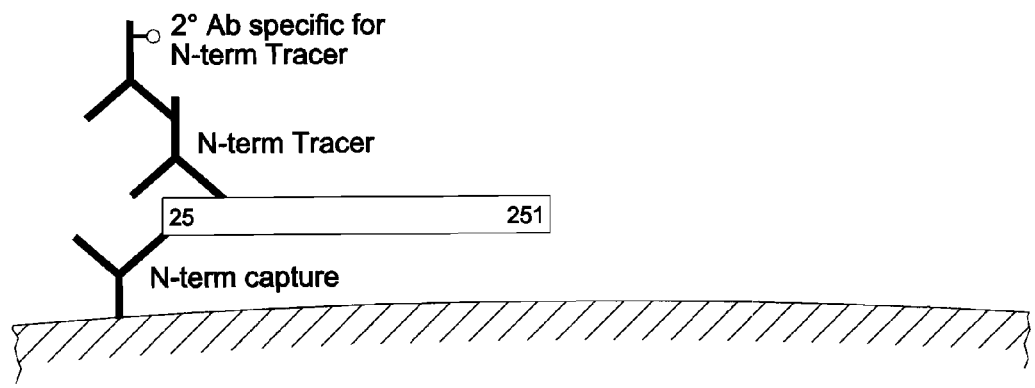
FIG. 36 is a side view of the C-terminal tracer antibody depicted in FIG. 35 showing a second antibody binding thereto, the second antibody having a separate label conjugated thereto for providing the indirect detection of the C-terminal sequence to which said C-terminal tracer antibody is bound.

Along those lines, and referring now to FIG. 36, there is shown an illustrative indirect method by which either of the respective N-terminal and C-terminal tracer antibodies can be detected following binding. In this regard, and as per conventional immunoassay technology, a secondary antibody having specificity for a specific tracer antibody, such as the C-terminal tracer antibody is shown. The second antibody, also conjugated with a label, will bind to the C-terminal tracer antibody and thus produce a signal corresponding to the degree of binding thereto. Such labeled secondary antibody will thus detect the degree of binding and thus may be utilized as per the other aforementioned labeling moieties to determine the presence and degree by which the respective tracer antibodies bind to the bound antigen.

Referring now to FIGS. 37-40, there is shown a second general format of the present invention whereby an immunoassay may be designed and configured pursuant to the teachings of the present invention to detect both intact FGF-23 and the C-terminal fragments thereof. As per the teachings discussed above with respect to FIGS. 32-35, such immunoassay operates on identical principles utilizing a capture antibody and two tracer antibodies for sequentially and/or separately detecting the intact FGF-23 and fragments thereof. In the embodiment illustrated in FIGS. 37-40, however, the capture antibody is operative to bind to the C-terminal region of FGF-23 (i.e., amino acids 180-251, SEQ ID NO.: 6), as opposed to the N-terminal of FGF-23.

According to a preferred embodiment, the C-terminal capture antibody will have an affinity for, and thus specifically bind to amino acids 186-206 or 225-244 of the C-terminal region of FGF-23.

Figure 37:
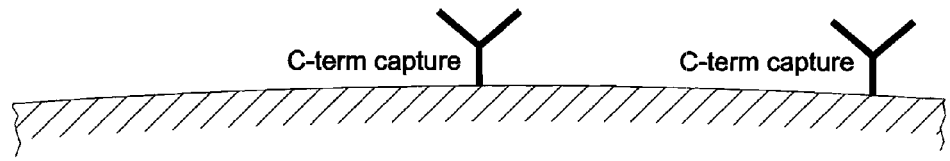
FIG. 37 is a side view of an immunoassay incorporating bound capture antibodies specific for the antigenic region formed upon a C-terminal region of FGF-23 as confined within amino acids 180-251 of FGF-23 (SEQ ID NO.: 4) wherein said antibodies operative to bind to intact FGF-23 and C-terminal fragments of FGF-23 present in a sample.
Figure 38:
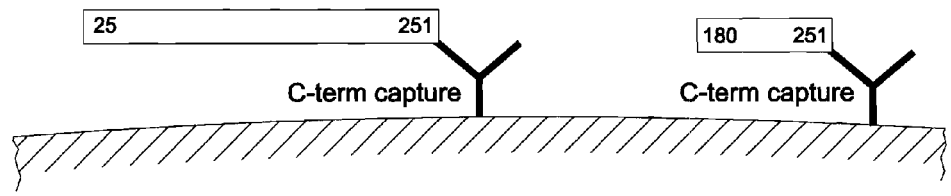
FIG. 38 is a side view of the assay of FIG. 37 depicting molecules of intact FGF-23 and C-terminal fragments thereof binding to the immobilized capture antibody.

As per the aforementioned embodiment, such C-terminal capture antibody is subjected to a sample suspected of containing both intact FGF-23 and fragments thereof as shown in FIG. 37. The intact FGF-23 and the C-terminal fragments thereof that possess an antigenic region to which the C-terminal capture antibody specifically binds, will thus become bound to the C-terminal capture antibody as illustrated in FIG. 38. A subsequent wash step will thus remove any fragments of FGF-23 not possessing the C-terminal antigenic region, including N-terminal fragments.

Figure 39:
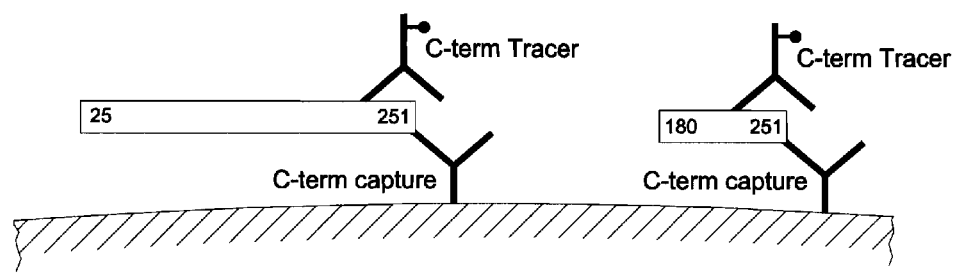
FIG. 39 is a side view of the assay depicted in FIGS. 37 and 38 showing a first tracer antibody having a label affixed thereto, said tracer antibody having an affinity for an antigenic region formed within amino acids 180-251 of FGF-23 (SEQ ID NO.: 4).

Thereafter, a tracer antibody specific for the C-terminal of FGF-23 will be introduced and will thus be operative to bind to the C-terminal region of FGF-23 as shown in FIG. 39. As discussed above, the specificity for the C-terminal tracer antibody will have an affinity for and specifically bind to an amino acid sequence dissimilar to that of the C-terminal capture antibody. The label affixed to the C-terminal tracer antibody will produce a signal corresponding to the degree of binding of the C-terminal tracer antibody to both the intact FGF-23 and the C-terminal fragments thereof, which will thus be measured by any of a variety of means known in the art.

Figure 40:
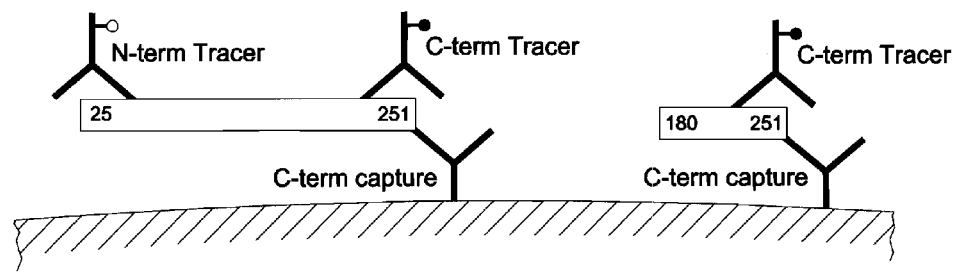
FIG. 40 is a side view of the assay depicted in FIGS. 37-39 showing a second tracer antibody having a label affixed thereto, said second tracer antibody having an affinity for an antigenic region within amino acids 25-179 of FGF-23 (SEQ ID NO.: 3).
Figure 41:
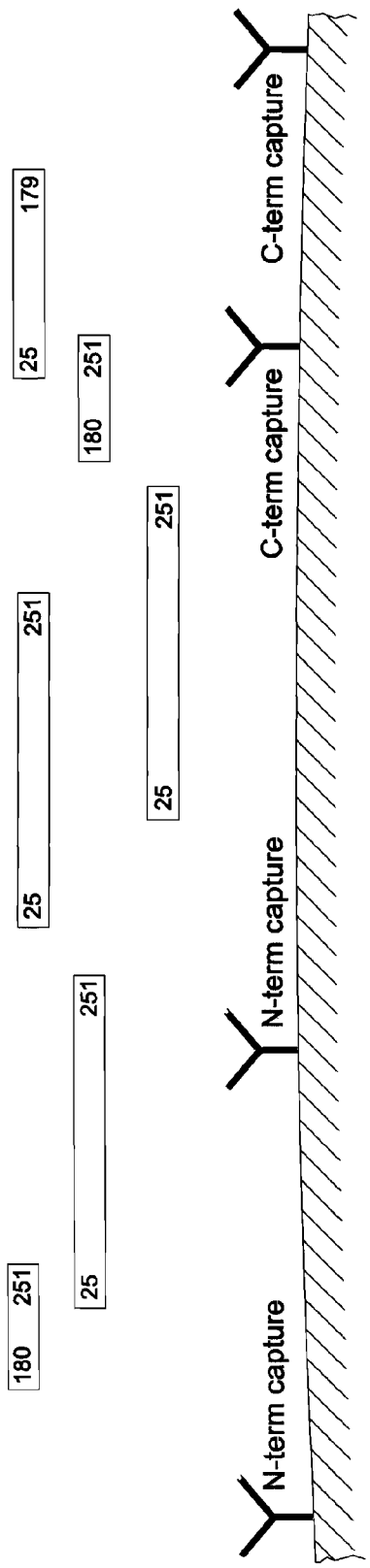
FIG. 41 is a side view of an immunoassay incorporating a combination of bound N-terminal capture antibodies having an affinity for an antigenic region formed between amino acids 25-179 of FGF-23 (SEQ ID NO.: 3) and C-terminal capture antibodies having an affinity for an antigenic region formed between amino acids 180-215 of FGF-23 (SEQ ID NO.: 6) and further depicting the introduction of a fluid sample having molecules of intact FGF-23 and N-terminal and C-terminal fragments of FGF-23 present therein.

As illustrated in FIG. 40, an N-terminal tracer antibody having a label conjugated thereto will then be introduced into the immunoassay and thus be operative to bind to intact FGF-23 having the N-terminal region containing the amino acid sequence to which the N-terminal tracer antibody will specifically bind. The label conjugated to the N-terminal tracer antibody will thus produce a signal corresponding to the degree of binding of the N-terminal tracer antibody, which is thus indicative of the presence and degree of only the intact FGF-23 molecules in the sample bound by the C-terminal capture antibody.

Per the aforementioned analysis, the degree of C-terminal fragments and intact FGF-23 can be readily determined. In this regard, and as discussed above, the labels affixed to the C-terminal and N-terminal tracer antibodies may be sequentially measured to determine the relative degree of binding or, alternatively, such labels may be dissimilar and thus operative to provide discrete and separate signals indicative of the degree of C-terminal and N-terminal binding by the respective tracer antibodies. Such tracer antibodies may also be detected via indirect methods via the use of secondary antibodies, as also discussed above.

With respect to either of the embodiments discussed above, it will be understood that the introduction of the N-terminal and C-terminal tracer antibodies may be sequentially introduced in either order, and need not necessarily be introduced in any specific order. In this regard, following incubation of the sample with either the C-terminal capture antibody or N-terminal capture antibody, either the C-terminal tracer antibody or N-terminal tracer antibody may next be introduced. In this regard, it is believed that the introduction of either tracer antibody will not affect the results produced by the immunoassays disclosed herein.

Referring now to FIGS. 41-45, there is shown a third format of an immunoassay constructed in accordance with a preferred embodiment of the present invention operative to detect intact FGF-23 and both the N-terminal and C-terminal fragments thereof that may be present in a sample. According to such embodiment with initial reference to FIG. 41, a combination of N-terminal capture antibodies and C-terminal capture antibodies are bound to a substrate. Per the other aforementioned embodiments, the N-terminal capture antibody is operative to bind to both intact FGF-23 and N-terminal fragments thereof having the antigenic sequence to which the N-terminal capture antibody has an affinity (i.e., the region within amino acids 25-179 to which it specifically binds). Similarly, the C-terminal capture antibody is operative to bind both intact FGF-23 and C-terminal fragments thereof that contain the antigenic sequence within amino acids 180-251 to which the C-terminal capture antibody will specifically bind.

Figure 42:
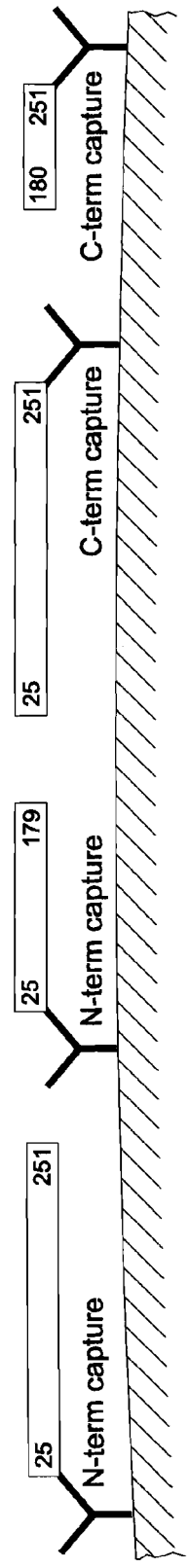
FIG. 42 is a side view of the immunoassay of FIG. 41 wherein said N-terminal capture antibodies are shown binding to both intact FGF-23 and said N-terminal fragments thereof and said C-terminal capture antibodies are shown binding to both intact FGF-23 and said C-terminal fragments thereof.
Figure 43:
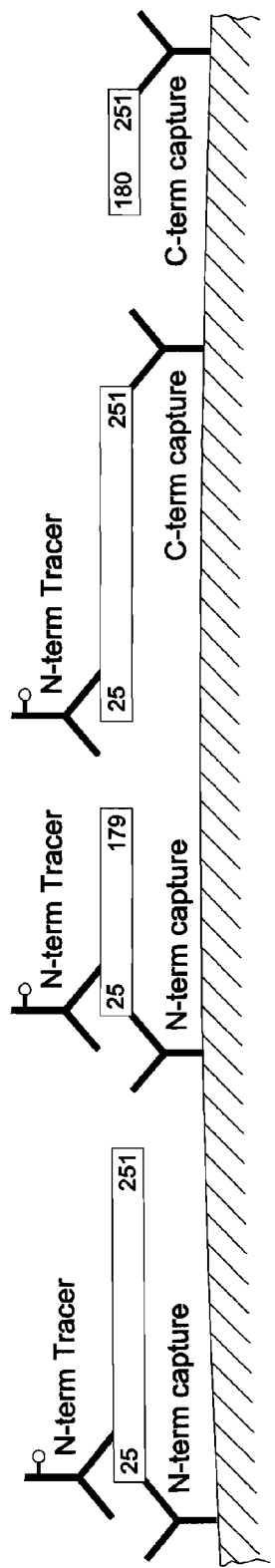
FIG. 43 is a side-view of the assay depicted in FIGS. 41 and 42 showing a first N-terminal tracer antibody having a label affixed thereto, said N-terminal tracer antibody having an affinity for an epitopic region formed within amino acids 25-179 of FGF-23 (SEQ ID NO.: 3) and operative to bind to the intact FGF-23 and N-terminal fragments thereof bound to said N-terminal capture antibody.
Figure 44:
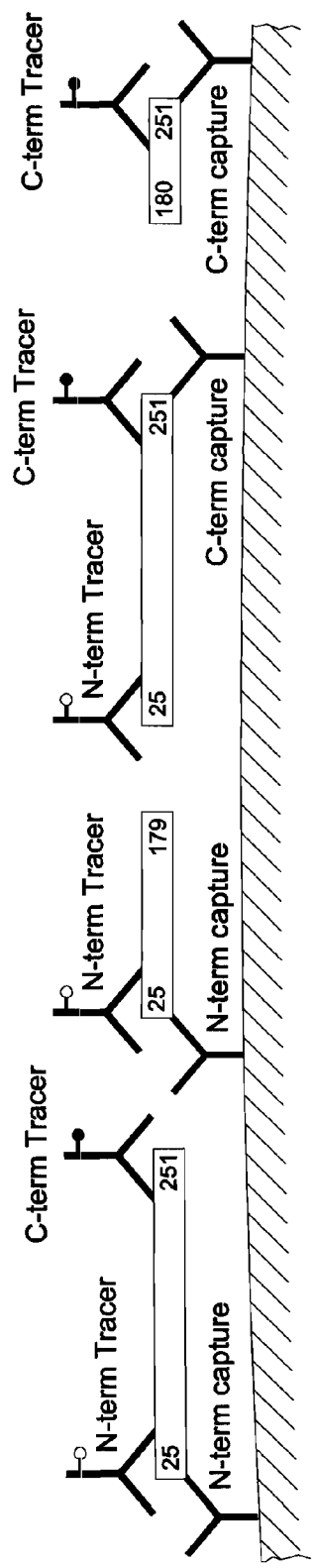
FIG. 44 is a side-view of the assay depicted in FIGS. 41-43 showing a second C-terminal tracer antibody having a label affixed thereto, said C-terminal tracer antibody having an affinity for an epitopic region formed within amino acids 180-251 of FGF-23 (SEQ ID NO.: 4) and operative to bind to the intact FGF-23 and N-terminal fragments thereof bound to said C-terminal capture antibody.
Figure 45:
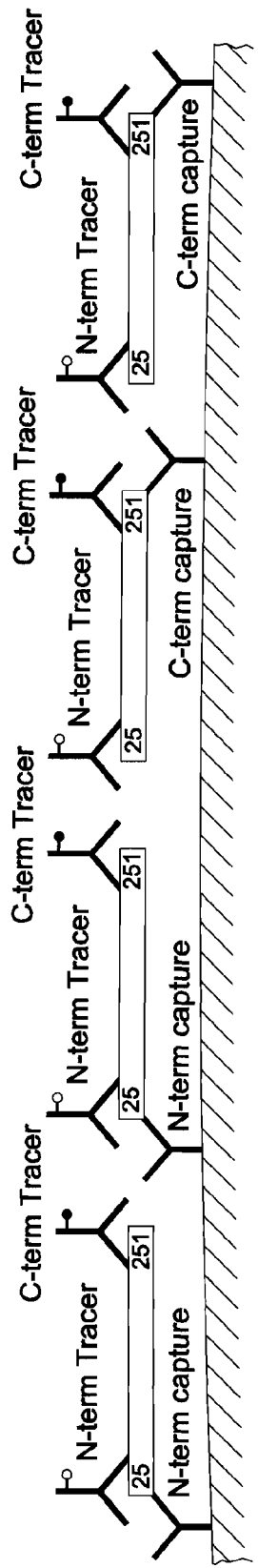
FIG. 45 is a side-view of the assay depicted in FIG. 44 illustrating the binding by the N-terminal and C-terminal tracer antibodies as would occur in a sample having primarily intact FGF-23 present in the sample such that both N-terminal and C-terminal tracer antibodies simultaneously bind to each intact FGF-23 molecule bound by each respective N-terminal and C-terminal capture antibody.

Following the introduction of a sample suspected of containing intact FGF-23 and fragments thereof, as illustrated in FIG. 42, the binding by the N-terminal capture antibodies and C-terminal capture antibodies are thus illustrated in FIG. 43-44.

After adequate incubation and a standard wash procedure, a labeled tracer antibody, which may be either an N-terminal tracer antibody or a C-terminal tracer antibody, is introduced to the immunoassay and operative to bind the specific antigenic sequences to which the tracer antibody has an affinity. In the embodiment shown in FIG. 43, the labeled N-terminal tracer antibody is first introduced and allowed to bind to the intact FGF-23 and N-terminal fragments thereof that are bound by the N-terminal capture antibody. A measurement of the signal produced by the label conjugated to the N-terminal tracer antibody thus provides a reading indicative of the degree of binding by the N-terminal tracer antibody, which will thus correspond to the total amount of intact FGF-23 as well as the N-terminal fragments that are bound. Along those lines, and as will be readily appreciated by those skilled in the art, the N-terminal tracer antibodies will bind to all bound intact FGF-23 molecules, including those bound to the C-terminal capture antibodies, due to the fact that the N-terminal region to which the N-terminal tracer antibody will bind will be present and thus operative to form a complex with the N-terminal tracer antibody.

A conventional wash step is then applied removing any excess labeled N-terminal tracer antibody and then the labeled C-terminal tracer antibody is introduced as illustrated in FIG. 44. The signal produced by the label conjugated to the C-terminal tracer antibody is then measured, which will correspond to the combined total of intact FGF-23 and C-terminal fragments thereof that are bound to the C-terminal capture antibody.

By measuring the degree and intensity of the signals produced by the respective labels conjugated to the N-terminal and C-terminal tracer antibodies, which as discussed above may be produced either by the sequential application of the tracer antibodies or, alternatively, may instead involve the simultaneous application using dissimilar labels conjugated to the respective N-terminal and C-terminal tracer antibodies, the presence and relative amounts of intact FGF-23 and both the N-terminal and C-terminal fragments thereof can be determined. Along those lines, it is believed that the relative amounts of the N-terminal and C-terminal capture antibodies can be selectively adjusted to target the relative amounts of a specific N-terminal or C-terminal fragment relative to intact FGF-23 that may be present in a given sample.

For example, to the extent it is desired to design an immunoassay that seeks to primarily detect C-terminal fragments of FGF-23, as opposed to intact FGF-23, which may be of particular importance in a variety of disease states and to monitor the degree of intact FGF-23 cleavage, a predominant amount of C-terminal capture antibodies relative N-terminal capture antibodies would be deployed. By doing so, both intact FGF-23 and the C-terminal fragments thereof are predominantly bound and thus capable of being detected. A diminished amount of activity produced by the N-terminal tracer antibody as utilized in such an assay would thus correspond to the lesser amount of intact FGF-23 present in such sample relative the captured and detected C-terminal fragments.

Similarly, for example, to the extent such an assay were to be designed to detect primarily intact FGF-23, which is an important, recognized biomarker of several diseases characterized by intact FGF-23 that is not effectively cleaved into its inactive fragments, generally equal amounts of N-terminal and C-terminal capture antibodies may be deployed. In such immunoassay, shown in FIG. 45, to the extent intact FGF-23 is primarily present, the signal strength produced by the labels conjugated to the C-terminal and N-terminal tracer antibodies would essentially be twice as robust as would occur to the extent only fragments of FGF-23 were present. In this regard, intact FGF-23 would be operative to bind both tracer antibodies, and thus produce twice the signaling capability as compared to separate N-terminal and C-terminal fragments of FGF-23, which would only bind to one respective N-terminal capture antibody or C-terminal capture antibody. Such immunoassays may further be designed through a variety of well-known techniques known in the art to achieve any of a variety of medical readings, as well as designed to selectively target any of a variety of antigenic regions on either the N-terminal or C-terminal region of FGF-23 sought to be detected and quantified.

In an alternative format, it is further contemplated that an assay can be readily designed per any of the aforementioned formats whereby all of the antibodies, both those directed to the C-terminal and N-terminal, are maintained in solution, as opposed to utilizing bound "capture" antibodies. In such format, it is contemplated that such antibodies may utilize dissimilar detection mechanisms, such as any of those discussed above, including indirect detection via secondary antibodies, or by the sequential application of the antibodies whereby the signaling strength imparted by the antibodies is thus indicative to the degree of binding of a specific N-terminal or C-terminal antibody to a target antigenic region on either the intact FGF-23 molecule or fragments thereof. Such "solution" type format advantageously allows for the aforementioned detection of both intact FGF-23 molecules and the N-terminal and C-terminal fragments thereof that do not initially require the "capture" antibodies to be physically bound upon a substrate. Such assay design would be well-known and readily understood by those skilled in the arts, and also readily operative to detect and quantify both intact FGF-23 and targeted fragments thereof.

Figure 46:
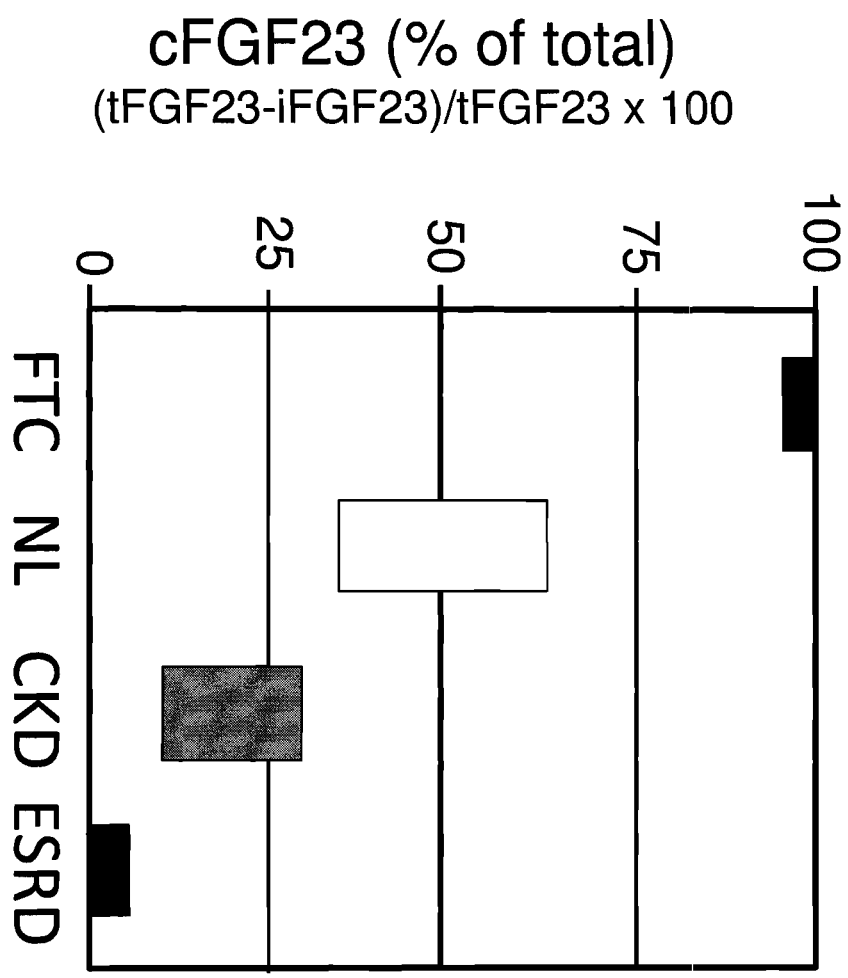
FIG. 46 is a graph depicting the ranges for the ratio of C-terminal FGF-23 fragments as a percentage of the combined presence of both C-terminal FGF-23 fragments and intact FGF-23 fragments in a sample, and how such percentage of C-terminal FGF-23 fragments relative the total combination of C-terminal fragments and intact FGF-23 fragments corresponds to both normal levels and specific disease states, including familial tumoral calcinosis (FTC), chronic kidney disease (CKD) and end stage renal disease (ESRD).

Along those lines, there is now known that several disease states are characterized by either elevated levels of FGF-23 relative to fragments thereof and vice versa. For example, autosomal dominant hypophosphatemic rickets (ADHR) and autosomal recessive hypophosphatemia (ARHP) are characterized by very high levels of FGF-23 relative to the fragments thereof. In contrast, familial tumoral calcinosis (FTC) is characterized by high levels of FGF-23 fragments. Other diseases, and in particular chronic kidney disease (CKD) and end stage renal disease (ESRD), are characterized by elevated levels of both intact FGF-23 and its fragments, in particular C-terminal fragments thereof whereby as the patients approach ESRD intact FGF-23 is the predominant form in circulation. To illustrate such distinctions, there is shown in FIG. 46 a table showing the relative percentage of C-terminal FGF-23 fragments as a percentage of the total FGF-23 in circulation (i.e., the sum of both intact FGF-23 and the fragments thereof minus the intact FGF-23 with such difference being divided by the total FGF-23 in circulation, then multiplied by 100) as a function of FTC, normal levels (NL), CKD and ESRD. It is likewise contemplated that as more research is conducted with respect to FGF-23 and the protein fragments of its catabolism, other correlations can be devised whereby the presence of a particular fragment of FGF-23 relative to intact FGF23 may serve as an important biological marker indicative of a particular disease state or condition.

Moreover, because it is understood that the particular form of FGF-23 that is present, and whether such form possesses biological activity and/or is cleaved into N-terminal and C-terminal fragments, it is contemplated that the immunoassays of the present invention may further be useful as a means of monitoring FGF-23 activity both from the standpoint of the presence and relative amounts of intact FGF-23 and fragments thereof, and how such components may change over time as may occur in connection with a particular disease, such as the progression of CKD to ESRD. Moreover, it is contemplated that the immunoassays of the present invention may be effective in monitoring and assessing potential therapeutic candidates that are operative to regulate the activity of FGF-23, which could potentially include but would not be limited to the rate at which intact FGF-23 is cleaved into inactive fragments. Other potential applications of the immunoassays of the present invention will further be readily apparent to those skilled in the art and capable of being designed and configured for a wide variety of applications related to the measurement of intact FGF-23 and the fragments thereof.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. An immunoassay method for simultaneously detecting in a single liquid sample intact FGF-23 molecules and C-terminal fragments thereof and further determining the ratio of said intact FGF-23 molecules to C-terminal fragments thereof in a liquid sample suspected of containing both intact FGF-23 molecules and C-terminal fragments thereof, said immunoassay method comprising the steps of:
   a) contacting said liquid sample with C-terminal capture antibodies, said C-terminal capture antibodies having a specificity for an antigenic region falling within amino acids 180-251 of FGF-23 (SEQ ID NO.: 4) such that substantially all intact FGF-23 molecules and substantially all C-terminal fragments having amino acids 180-251 (SEQ ID NO.: 4) are bound thereto;
   b) contacting said intact FGF-23 molecules and C-terminal fragments with C-terminal tracer antibodies having a label conjugated thereto, each said C-terminal tracer antibody being specific for an antigenic sequence falling within amino acids 180-251 of FGF-23 (SEQ ID NO.: 4), said specificity of said C-terminal tracer antibody being dissimilar to said specificity of said C-terminal capture antibodies such that in use, a C-terminal capture antibody and a C-terminal tracer antibody simultaneously bind to an intact FGF-23 molecule and/or a C-terminal fragment;
   c) measuring a first signal generated by said label conjugated to said C-terminal tracer antibodies bound in step b), said first signal being indicative of the degree of binding of said C-terminal tracer antibodies to both said intact FGF-23 molecules and said C-terminal fragments;
   d) simultaneously with step b), contacting said intact FGF-23 molecules and C-terminal fragments thereof with N-terminal tracer antibodies having a label conjugated thereto, said N-terminal tracer antibodies having an affinity for and specifically binding to an antigenic region formed within amino acids 25-179 of FGF-23 (SEQ ID NO.: 3), each N-terminal tracer antibody being able to bind to said antigenic region sequentially or simultaneously in combination with said C-terminal tracer antibody and said C-terminal capture antibody, said label conjugated to said N-terminal tracer antibody producing a second signal corresponding to only the intact FGF-23 molecules bound by said C-terminal capture antibody;
   e) measuring the second signal produced by said labels of said N-terminal tracer antibodies of step d), said second signal being indicative of only the intact FGF-23 molecules present in said liquid sample; and
   f) comparing the measured value of the first signal measured in step c) to the measured value of the second signal measured in step e), the result of the comparison being indicative of the ratio of intact FGF-23 molecules to C-terminal fragments thereof in said single liquid sample.

2. The immunoassay method of claim 1 wherein in step b) and d) said label conjugated to said C-terminal tracer antibodies and said N-terminal tracer antibodies are selected from the group consisting of radioisotope label, a fluorescent label, an enzymatic label and dye-type label.

3. The immunoassay method of claim 1 wherein said label conjugated to said C-terminal tracer antibody is dissimilar to said label conjugated to said N-terminal tracer antibody.

4. An immunoassay method for simultaneously detecting in a single liquid sample intact FGF-23 molecules and N-terminal fragments thereof and further determining the ratio of said intact FGF-23 molecules to N-terminal fragments thereof in a liquid sample suspected of containing both intact FGF-23 molecules and N-terminal fragments thereof, said immunoassay method comprising the steps of:
   a) contacting said liquid sample with N-terminal capture antibodies, said N-terminal capture antibodies having a specificity for an antigenic region falling within amino acids 25-179 of FGF-23 (SEQ ID No.: 3) such that substantially all intact FGF-23 molecules and substantially all N-terminal fragments having amino acids 25-179 (SEQ ID NO.: 3) are bound thereto;
   b) simultaneously with step a), contacting said intact FGF-23 molecules and N-terminal fragments with N-terminal tracer antibodies having a label conjugated thereto, each said N-terminal tracer antibody being specific for an antigenic sequence falling within amino acids 25-179 of FGF-23, said specificity of said N-terminal tracer antibody being dissimilar to said specificity of said N-terminal capture antibodies such that in use, an N-terminal capture antibody and an N-terminal tracer antibody are capable of simultaneously binding to an intact FGF-23 molecule or an N-terminal fragment;
   c) measuring a first signal generated by said label conjugated to said N-terminal antibody bound in step b), said first signal being indicative of the degree of binding of said N-terminal tracer antibody to both said intact FGF-23 molecules and said N-terminal fragments;
   d) simultaneously with step b), contacting said intact FGF-23 molecules and N-terminal fragments thereof with C-terminal tracer antibodies having a label conjugated thereto, said C-terminal tracer antibodies having an affinity for and specifically binding to an antigenic region formed within amino acids 180-251 of FGF-23 (SEQ ID NO.: 4), each C-terminal tracer antibody being able to bind to said antigenic region sequentially or simultaneously in combination with said N-terminal tracer antibody and said N-terminal capture antibody, said label conjugated to said C-terminal tracer antibody producing a signal corresponding to only the intact FGF-23 molecules bound by said N-terminal capture antibody; and
   e) measuring a second signal produced by said label of said C-terminal tracer antibody of step d), said second signal being indicative of only the intact FGF-23 molecules present in said liquid sample;
   f) comparing the measured value of the first signal measured in step c) to the measured value of the second signal measured in step e), the result of the comparison being indicative of the ratio of intact FGF-23 molecules to N-terminal fragments thereof in said single liquid sample.

5. The immunoassay method of claim 4 wherein in step b) and d) said label conjugated to said N-terminal tracer antibodies and said C-terminal tracer antibodies are selected from the group consisting of radioisotope label, a fluorescent label, an enzymatic label and dye-type label.

6. The immunoassay method of claim 4 wherein said label conjugated to said N-terminal tracer antibody is dissimilar to said label conjugated to said C-terminal tracer antibody.

7. An immunoassay method for simultaneously detecting in a single liquid sample intact FGF-23 molecules and the N-terminal and C-terminal fragments thereof and further determining the ratios of said intact FGF-23 molecules to the N-terminal and C-terminal fragments thereof in a liquid sample suspected of containing intact FGF-23 molecules, N-terminal fragments thereof, and C-terminal fragments thereof, said immunoassay method comprising the steps of:

a) simultaneously contacting said liquid sample with N-terminal and C-terminal capture antibodies, said N-terminal capture antibodies and C-terminal capture antibodies being present in a predetermined fixed proportion to one another, said C-terminal capture antibodies having a specificity for an antigenic region falling within amino acids 180-251 of FGF-23 (SEQ ID No.: 4) such that intact FGF-23 molecules and C-terminal fragments having amino acids 180-251 (SEQ ID NO.: 4) can bind thereto, said N-terminal capture antibodies having a specificity for an antigenic region falling within amino acids 25-179 (SEQ ID No.: 3) of FGF-23 such that intact FGF-23 molecules and N-terminal fragments having amino acids 25-179 (SEQ ID NO.: 3) can bind thereto;

b) contacting said intact FGF-23 molecules and C-terminal fragments bound to said C-terminal capture antibodies in step a) with C-terminal tracer antibodies having a C-terminal label conjugated thereto, said C-terminal tracer antibodies being specific for an antigenic sequence falling within amino acids 180-251 of FGF-23 (SEQ ID NO.: 4), said specificity of said C-terminal tracer antibodies being dissimilar to said specificity of said C-terminal capture antibodies such that in use, each said C-terminal capture antibody and said C-terminal tracer antibody can simultaneously bind to said intact FGF-23 molecules and said C-terminal fragments;

c) simultaneously with step b), contacting said intact FGF-23 molecules and N-terminal fragments bound to said N-terminal capture antibodies in step a) with a N-terminal tracer antibody having an N-terminal label conjugated thereto, said N-terminal tracer antibodies being specific for an antigenic sequence falling within amino acids 25-179 of FGF-23 (SEQ ID NO.: 3), said specificity of said N-terminal tracer antibodies being dissimilar to said specificity of said N-terminal capture antibodies such that in use, each said N-terminal capture antibody and said N-terminal tracer antibody can simultaneously bind to said intact FGF-23 molecules and said N-terminal fragments;

d) measuring a C-terminal signal generated by said C-terminal label conjugated to said C-terminal tracer antibody bound in step b);

e) measuring an N-terminal signal generated by said N-terminal label conjugated to said N-terminal tracer antibody bound in step c);

f) comparing the measured value of the C-terminal signal measured in step d, the measured value of the N-terminal signal measured in step e, and the predetermined fixed proportion of C-terminal and N-terminal capture antibodies, the result of the comparison being indicative of the ratios of intact FGF-23 molecules, C-terminal fragments thereof, and N-terminal fragments thereof in said single liquid sample.

* * * * *

SEQUENCE LISTING

```
<160> NUMBER OF SEQ ID NOS: 31

<210> SEQ ID NO 1
<211> LENGTH: 251
<212> TYPE: PRT
<213> ORGANISM: Homo sapiens

<400> SEQUENCE: 1

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60
```

```
Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                 85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 2
<211> LENGTH: 227
<212> TYPE: PRT
<213> ORGANISM: Homo sapiens

<400> SEQUENCE: 2

Tyr Pro Asn Ala Ser Pro Leu Leu Gly Ser Ser Trp Gly Gly Leu Ile
 1               5                  10                  15

His Leu Tyr Thr Ala Thr Ala Arg Asn Ser Tyr His Leu Gln Ile His
                 20                  25                  30

Lys Asn Gly His Val Asp Gly Ala Pro His Gln Thr Ile Tyr Ser Ala
             35                  40                  45

Leu Met Ile Arg Ser Glu Asp Ala Gly Phe Val Val Ile Thr Gly Val
         50                  55                  60

Met Ser Arg Arg Tyr Leu Cys Met Asp Phe Arg Gly Asn Ile Phe Gly
 65                  70                  75                  80

Ser His Tyr Phe Asp Pro Glu Asn Cys Arg Phe Gln His Gln Thr Leu
                 85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190
```

```
Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
        210                 215                 220

Lys Phe Ile
225

<210> SEQ ID NO 3
<211> LENGTH: 155
<212> TYPE: PRT
<213> ORGANISM: Homo sapiens

<400> SEQUENCE: 3

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
130                 135                 140

Phe Asn Thr Pro Ile Pro Arg Arg His Thr Arg
145                 150                 155

<210> SEQ ID NO 4
<211> LENGTH: 72
<212> TYPE: PRT
<213> ORGANISM: Homo sapiens

<400> SEQUENCE: 4

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
            20                  25                  30

Ser Ala Glu Asp Asn Ser Pro Met Ala Ser Asp Pro Leu Gly Val Val
        35                  40                  45

Arg Gly Gly Arg Val Asn Thr His Ala Gly Gly Thr Gly Pro Glu Gly
50                  55                  60

Cys Arg Pro Phe Ala Lys Phe Ile
65                  70

<210> SEQ ID NO 5
<211> LENGTH: 18
<212> TYPE: PRT
<213> ORGANISM: Homo sapiens

<400> SEQUENCE: 5
```

-continued

Tyr Pro Asn Ala Ser Pro Leu Leu Gly Ser Ser Trp Gly Gly Leu Ile
1               5                   10                  15

His Leu

<210> SEQ ID NO 6
<211> LENGTH: 45
<212> TYPE: PRT
<213> ORGANISM: Homo sapiens

<400> SEQUENCE: 6

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile
        35                  40                  45

<210> SEQ ID NO 7
<211> LENGTH: 76
<212> TYPE: PRT
<213> ORGANISM: Homo sapiens

<400> SEQUENCE: 7

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly
65                  70                  75

<210> SEQ ID NO 8
<211> LENGTH: 150
<212> TYPE: PRT
<213> ORGANISM: Homo sapiens

<400> SEQUENCE: 8

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
            85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
        130                 135                 140

Phe Asn Thr Pro Ile Pro
145                 150

<210> SEQ ID NO 9
<211> LENGTH: 16
<212> TYPE: PRT
<213> ORGANISM: Homo sapiens

<400> SEQUENCE: 9

His Leu Tyr Thr Ala Thr Ala Arg Asn Ser Tyr His Leu Gln Ile His
1               5                   10                  15

<210> SEQ ID NO 10
<211> LENGTH: 19
<212> TYPE: PRT
<213> ORGANISM: Homo sapiens

<400> SEQUENCE: 10

Tyr His Leu Gln Ile His Lys Asn Gly His Val Asp Gly Ala Pro His
1               5                   10                  15

Gln Thr Ile

<210> SEQ ID NO 11
<211> LENGTH: 24
<212> TYPE: PRT
<213> ORGANISM: Homo sapiens

<400> SEQUENCE: 11

Asn Gly His Val Asp Gly Ala Pro His Gln Thr Ile Tyr Ser Ala Leu
1               5                   10                  15

Met Ile Arg Ser Glu Asp Ala Gly
            20

<210> SEQ ID NO 12
<211> LENGTH: 17
<212> TYPE: PRT
<213> ORGANISM: Homo sapiens

<400> SEQUENCE: 12

Pro His Gln Thr Ile Tyr Ser Ala Leu Met Ile Arg Ser Glu Asp Ala
1               5                   10                  15

Gly

<210> SEQ ID NO 13
<211> LENGTH: 16
<212> TYPE: PRT
<213> ORGANISM: Homo sapiens

<400> SEQUENCE: 13

Tyr Ser Ala Leu Met Ile Arg Ser Glu Asp Ala Gly Phe Val Val Ile
1               5                   10                  15

<210> SEQ ID NO 14
<211> LENGTH: 17
<212> TYPE: PRT
<213> ORGANISM: Homo sapiens

<400> SEQUENCE: 14

Val Ile Thr Gly Val Met Ser Arg Arg Tyr Leu Cys Met Asp Phe Arg
1               5                   10                  15

Gly

```
<210> SEQ ID NO 15
<211> LENGTH: 26
<212> TYPE: PRT
<213> ORGANISM: Homo sapiens

<400> SEQUENCE: 15

Ser Arg Arg Tyr Leu Cys Met Asp Phe Arg Gly Asn Ile Phe Gly Ser
1               5                   10                  15

His Tyr Phe Asp Pro Glu Asn Cys Arg Phe
            20                  25

<210> SEQ ID NO 16
<211> LENGTH: 21
<212> TYPE: PRT
<213> ORGANISM: Homo sapiens

<400> SEQUENCE: 16

Gly Asn Ile Phe Gly Ser His Tyr Phe Asp Pro Glu Asn Cys Arg Phe
1               5                   10                  15

Gln His Gln Thr Leu
            20

<210> SEQ ID NO 17
<211> LENGTH: 21
<212> TYPE: PRT
<213> ORGANISM: Homo sapiens

<400> SEQUENCE: 17

Pro Glu Asn Cys Arg Phe Gln His Gln Thr Leu Glu Asn Gly Tyr Asp
1               5                   10                  15

Val Tyr His Ser Pro
            20

<210> SEQ ID NO 18
<211> LENGTH: 11
<212> TYPE: PRT
<213> ORGANISM: Homo sapiens

<400> SEQUENCE: 18

Thr Leu Glu Asn Gly Tyr Asp Val Tyr His Ser
1               5                   10

<210> SEQ ID NO 19
<211> LENGTH: 21
<212> TYPE: PRT
<213> ORGANISM: Homo sapiens

<400> SEQUENCE: 19

Pro Gln Tyr His Phe Leu Val Ser Leu Gly Arg Ala Lys Arg Ala Phe
1               5                   10                  15

Leu Pro Gly Met Asn
            20

<210> SEQ ID NO 20
<211> LENGTH: 21
<212> TYPE: PRT
<213> ORGANISM: Homo sapiens

<400> SEQUENCE: 20

Arg Ala Lys Arg Ala Phe Leu Pro Gly Met Asn Pro Pro Pro Tyr Ser
1               5                   10                  15

Gln Phe Leu Ser Arg
```

<210> SEQ ID NO 21
<211> LENGTH: 21
<212> TYPE: PRT
<213> ORGANISM: Homo sapiens

<400> SEQUENCE: 21

Asn Pro Pro Tyr Ser Gln Phe Leu Ser Arg Arg Asn Glu Ile Pro
1               5                   10                  15

Leu Ile His Phe Asn
            20

<210> SEQ ID NO 22
<211> LENGTH: 15
<212> TYPE: PRT
<213> ORGANISM: Homo sapiens

<400> SEQUENCE: 22

Arg Arg Asn Glu Ile Pro Leu Ile His Phe Asn Thr Pro Ile Pro
1               5                   10                  15

<210> SEQ ID NO 23
<211> LENGTH: 27
<212> TYPE: PRT
<213> ORGANISM: Homo sapiens

<400> SEQUENCE: 23

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys
            20                  25

<210> SEQ ID NO 24
<211> LENGTH: 21
<212> TYPE: PRT
<213> ORGANISM: Homo sapiens

<400> SEQUENCE: 24

Glu Arg Asp Pro Leu Asn Val Leu Lys Pro Arg Ala Arg Met Thr Pro
1               5                   10                  15

Ala Pro Ala Ser Cys
            20

<210> SEQ ID NO 25
<211> LENGTH: 59
<212> TYPE: PRT
<213> ORGANISM: Homo sapiens

<400> SEQUENCE: 25

Glu Arg Asp Pro Leu Asn Val Leu Lys Pro Arg Ala Arg Met Thr Pro
1               5                   10                  15

Ala Pro Ala Ser Cys Ser Gln Glu Leu Pro Ser Ala Glu Asp Asn Ser
            20                  25                  30

Pro Met Ala Ser Asp Pro Leu Gly Val Val Arg Gly Gly Arg Val Asn
        35                  40                  45

Thr His Ala Gly Gly Thr Gly Pro Glu Gly Cys
        50                  55

<210> SEQ ID NO 26
<211> LENGTH: 17
<212> TYPE: PRT

<213> ORGANISM: Homo sapiens

<400> SEQUENCE: 26

Cys Ser Gln Glu Leu Pro Ser Ala Glu Asp Asn Ser Pro Met Ala Ser
1               5                   10                  15
Asp

<210> SEQ ID NO 27
<211> LENGTH: 39
<212> TYPE: PRT
<213> ORGANISM: Homo sapiens

<400> SEQUENCE: 27

Cys Ser Gln Glu Leu Pro Ser Ala Glu Asp Asn Ser Pro Met Ala Ser
1               5                   10                  15

Asp Pro Leu Gly Val Val Arg Gly Gly Arg Val Asn Thr His Ala Gly
            20                  25                  30

Gly Thr Gly Pro Glu Gly Cys
        35

<210> SEQ ID NO 28
<211> LENGTH: 20
<212> TYPE: PRT
<213> ORGANISM: Homo sapiens

<400> SEQUENCE: 28

Gly Val Val Arg Gly Gly Arg Val Asn Thr His Ala Gly Gly Thr Gly
1               5                   10                  15

Pro Glu Gly Cys
        20

<210> SEQ ID NO 29
<211> LENGTH: 27
<212> TYPE: PRT
<213> ORGANISM: Homo sapiens

<400> SEQUENCE: 29

Gly Val Val Arg Gly Gly Arg Val Asn Thr His Ala Gly Gly Thr Gly
1               5                   10                  15

Pro Glu Gly Cys Arg Pro Phe Ala Lys Phe Ile
            20                  25

<210> SEQ ID NO 30
<211> LENGTH: 22
<212> TYPE: PRT
<213> ORGANISM: Homo sapiens

<400> SEQUENCE: 30

Gly Arg Val Asn Thr His Ala Gly Gly Thr Gly Pro Glu Gly Cys Arg
1               5                   10                  15

Pro Phe Ala Lys Phe Ile
            20

<210> SEQ ID NO 31
<211> LENGTH: 12
<212> TYPE: PRT
<213> ORGANISM: Homo sapiens

<400> SEQUENCE: 31

Gly Pro Glu Gly Cys Arg Pro Phe Ala Lys Phe Ile
1               5                   10